United States Patent [19]

Heinze et al.

[11] Patent Number: 5,334,351
[45] Date of Patent: Aug. 2, 1994

[54] SENSOR FOR DETECTING ANALYTES IN A FLUID MEDIUM

[75] Inventors: Jürgen Heinze, Freiburg; Andreas W. Synowczyk, Bad Krozingen, both of Fed. Rep. of Germany

[73] Assignee: Drägerwerk Aktiengesellschaft, Lübeck, Fed. Rep. of Germany

[21] Appl. No.: 81,127

[22] Filed: Jun. 25, 1993

[30] Foreign Application Priority Data

Jun. 27, 1992 [DE] Fed. Rep. of Germany ....... 4221233
Dec. 10, 1992 [DE] Fed. Rep. of Germany ....... 4241438

[51] Int. Cl.$^5$ .................... G01N 27/00; G01N 31/00
[52] U.S. Cl. ........................ 422/90; 422/98; 436/106; 436/113
[58] Field of Search ............... 422/82.02, 82.01, 90, 422/98; 436/113, 106

[56] References Cited

FOREIGN PATENT DOCUMENTS 0398286 11/1990 European Pat. Off. .
4114536 11/1991 Fed. Rep. of Germany .

OTHER PUBLICATIONS

Guo et al., "Doping Bucky: Formation and Properties of Boron-Doped Buckminsterfullerene" *J. Phys. Chem.* vol. 95, No. 13, pp. 4948–4950, Jul. 1991.

Zhov et al.; "Reduction and Electrochemistry of $C_{60}$ in Liquid Ammonia," J. Ame. Chem. Soc. 1992, 114, 11004–11006.

Petrie et al.; "Derivatization of fullerene de-cations $C^{60+2}$ and $C_{70}^{+20}$ by Ion-Molecule reactions in gas phase"; J. Am. Chem. Soc. 1992, 114, 9177–9181.

Stay et al.; "Novel-Ion Molecule reactions of $C_{60}^{+2}$ with NHz"; J. Am. Soc. Chem., 1992, 114, 7914–7916.

Pradeep et al.; "Interaction of nitrogen with fullerenes: Nitrogen derivatives of $C_{60}$ and $C_{70}$"; J. Phys. Chem., 1991, 95, 10564–10565.

Chai et al.; "Fullerenes with metals inside"; J. Phys. Chem. 1991, 95, 7564–7568.

*Primary Examiner*—Robert J. Warden
*Assistant Examiner*—Robert Carpenter
*Attorney, Agent, or Firm*—Walter Ottesen

[57] ABSTRACT

A sensor detects analytes in a fluid medium by measuring the conductivity of a layer on a carrier with the layer contacting an electrode pair. The layer interacts with the analyte and is improved in that the sensor has a long-term stability and the indication provided by the sensor is completely reversible. The layer is a fullerene layer.

17 Claims, 1 Drawing Sheet

SENSOR FOR DETECTING ANALYTES IN A FLUID MEDIUM

FIELD OF THE INVENTION

The invention relates to a sensor for detecting analytes in a fluid medium by measuring the conductivity of a layer on a carrier. The layer is in contact with an electrode pair and interacts with the analytes.

BACKGROUND OF THE INVENTION

European patent publication 0,398,286 discloses a gas sensor for detecting ammonia. The gas sensor has an interdigitated electrode pair on a ceramic carrier and the gap between the electrodes is covered by a layer of polyaniline. The change of the electric resistance between the electrodes of the gas sensor is caused by the interaction of the ammonia with the polyaniline layer and is a measure of the ammonia concentration to be detected.

It is a disadvantage of this known gas sensor that it has insufficient long-term stability and that the indication provided thereby is not completely reversible.

Published German patent application 4,114,536 discloses special cage-like carbon molecule structures which can be characterized as so-called fullerenes. Fullerenes comprise a triple coordinated aromatic carbon with the molecules being composed exclusively of pentacycles and hexacycles, that is, the molecules have especially stable structures. All fullerenes contain twelve pentacycles and (n) hexacycles with (n) being an even number greater than or equal to zero. The number (x) of the carbon atoms of a fullerene molecule results from the number (n) of the hexacycles. The number (x) is given by: $x=2(n)+20$. $C_{60}$ fullerene and $C_{70}$ fullerene should be mentioned in this context. The $C_{60}$ fullerene has a precisely spherical-shaped structure with 20 hexagons on the surface and the $C_{70}$ fullerene has 25 hexagons.

$C_{60}$ and $C_{70}$ fullerenes are significant for the practical application since they are especially simple to produce. For example, graphite is converted into $C_{60}$ and $C_{70}$ fullerenes to a certain proportion with a resistance heating in a helium atmosphere.

Detectable analytes can be organic analytes such as alkenes, alkynes and aromatic hydrocarbons or inorganic analytes such as ammonia, hydrazine, phosphine, $H_2S$ and halogens.

SUMMARY OF THE INVENTION

It is an object of the invention to provide a sensor of the kind described above which is improved so that the sensor has a high long-term stability and wherein the interaction taking place in the layer with the analyte to be detected is completely reversible.

According to a feature of the invention, the layer of the sensor is a fullerene layer. The invention is based on the unexpectedly found fact that an analyte interacts with the layer made of fullerene in the manner of an electron exchange so that the electric conductivity is changed in accordance with the concentration or composition of the analyte in the fluid medium. The above-mentioned fullerene layer is disposed on an electrode pair. An electron exchange is, for example, possible when the analyte is present in the fluid medium as an electron donor. Experiments have shown that this interaction is completely reversible so that the sensor according to the invention has a very long service life.

The reversibility of the indication provided by the sensor is based on the especially stable molecular structure of the fullerenes. The fluid medium with the analytes to be detected can be present in the form of gases, vapors or liquids.

It is advantageous to admix a substance facilitating the interaction to the fluid medium and/or to the analyte and/or to the fullerene. The interaction within the fullerene layer can be increased as experiments have shown, for example, by means of protons attached to the surface of the fullerene molecule. It has been shown to be advantageous when the analyte to be detected and the fullerene have a similar proton affinity or when the proton affinity is produced or adjusted with the aid of admixed substances.

A substance which can usefully admixed is water or water vapor since protons attach especially well to fullerenes.

A useful adaptation of the fullerene to the fluid to be detected can take place by metal doping the fullerene. Useful substances are alkali metals and alkaline earth metals. It is advantageous to provide the interdigitated electrode pair with a layer of $C_{60}$ and/or $C_{70}$ fullerenes. The fullerenes can be present in pure form as $C_{60}$ or $C_{70}$ fullerenes or as a mixture. A useful mixture ratio comprises, for example, 75% $C_{60}$ and 23% $C_{70}$. The remaining portion of 2% comprises higher valance fullerenes or graphite which occur during production. An interdigitated configuration is especially useful as an embodiment of the electrode pair.

It is useful that the layer comprises tetrahedral-symmetrical and/or octahedral-symmetrical and/or icosahedral-symmetrical fullerenes and/or the fullerenes are present as neutralized geometric tripoles or neutralized dipoles. Homogeneous geometric structures having molecules of a fixed number of carbon atoms as well as also mixed structures are suitable for a layer. The mixed structures are composed of higher valance and lower valance fullerenes.

A useful thickness of the layer is greater than approximately 0.1 microgram per square centimeter.

In an advantageous manner, the electrode pair can be connected to a resistance measuring bridge or constant current or constant voltage source for measurement.

Analytes suitable to be detected are substances which have a characteristic such that the substance makes possible an exchange of electrons. This characteristic influences the electric conductivity of the layer. Useful analytes having the characteristic of an electron donor are ammonia and derivatives thereof such as amines, hydrazine, phosphine, arsine and hydrogen sulfide.

A useful method for producing a layer from a fullerene for the sensor of the invention comprises dissolving the fullerene in a suspension of methylene chloride or benzene and then applying the layer to the electrode pair by dip coating, spray coating or spin coating.

The electrical characteristics of fullerene molecule structures can be changed by doping or substitution in such a manner that a plurality of analytes can be detected. Analytes which can be detected are organic analytes such as alkenes, alkynes, amines, aromatic hydrocarbons (benzene, toluene), alcohol (ethanol, propanol), carbonyl compounds (acetone, formaldehyde), halogenated hydrocarbons (perchloroethylene), heterocyclene (thiophene), thiols, sulfides and nitrogen compounds and inorganic analytes such as ammonia, hydrazine, phosphine, arsine, $H_2S$, halogens ($Cl_2$, $Br_2$), nitrogen oxide and water.

The sensitivity of a doped or substituted fullerene molecule structure with respect to the analyte to be detected is dependent upon the charge state of the fullerene molecule, the counter ion and the number of carbon atoms of the fullerene base molecule utilized.

Doping of the fullerene molecules can be realized, for example, by electrochemical reduction or with the aid of suitable chemical reducing agents. In this way, a doped fullerene layer can be produced by electrochemical deposits of the trianion from a solution of $C_{60}/C_{70}$ fullerene in methylene chloride ($CH_2Cl_2$) with $TBAPF_6$ as a conductive electrolyte on the surface of an electrode pair.

Possible reducing agents for doping a fullerene molecule are Na, K, (tetraphenylporphyrinato) chrome (II) and cobaltocene.

The following fullerene derivatives can be used as substituted fullerenes, for example:

| | | |
|---|---|---|
| $C_{60}NR_2R')_x$ | R = alkyl, aryl | R' = alkyl, aryl, H |
| $C_{60}(PR_2R')_x$ | | x = 6, 12 |
| $C_{60}H_y$ | | y = (12, 24), 36 |
| $C_{60}Cl_n$ | | n = 26 |
| $C_{60}Br_4$ | | |

An advantageous method for producing a doped fullerene layer sensitive to toxic substances comprises first producing a saturated solution of $C_{60}/C_{70}$ fullerene in methylene chloride in an electrochemical measuring cell at a temperature of approximately $-20°$ C. in an atmosphere of inert gas with $TBAPF_6$ being added as a conductive electrolyte. Thereafter, the fullerene layer is applied electrolytically at a potential of the fullerene trianion to a gold coated interdigitated electrode pair. During the electrolysis, a red-brown film deposits as a doped fullerene layer on the surface of the electrode pair. After the electrolysis, rinsing is performed with methylene chloride and then dried. The doped $C_{60}/C_{70}$ fullerene layer according to the invention allows, for example, chlorine ($Cl_2$) as a toxic substance to be detected. Experiments have shown that the interaction between the layer and the toxic substance to be detected is completely reversible.

The sensor can be a discrete component having an interdigitated electrode pair with the fullerene layer or as a so-called sensor array having several interdigitated structures on a carrier. Different fullerene layers can be applied to the sensor array which can be matched to the analytes to be detected.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
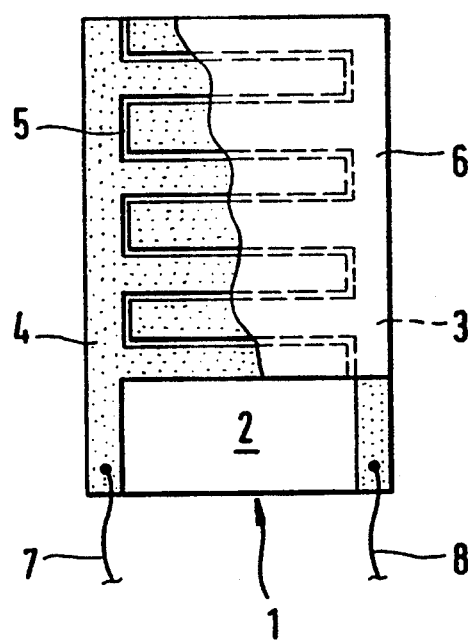
FIG. 1 is a plan view of a sensor having a layer.

FIG. 1 shows a sensor 1 comprising a carrier 2 made of ceramic on which an electrode pair (3, 4) is arranged as an interdigitated structure. The electrode pair (3, 4) is identified below as electrodes (3, 4) and usefully comprises a gold layer which is sputtered onto the carrier 2 and a gap 5 between the electrodes (3, 4). The electrodes (3, 4) and the gap 5 are covered by a fullerene layer 6. Contact is made to the electrodes (3, 4) by means of connecting leads (7, 8), respectively, which are connected to an evaluation unit shown in FIG. 2.

The fullerene layer 6 is produced in such a manner that a mixture of approximately 70% $C_{60}$ and 30% $C_{70}$ fullerene is dissolved in benzene and the fullerene is then applied in a dip-coating process to the electrodes (3, 4) disposed on the carrier 2.

If the sensor is subjected to a moist ammonia gas, then a change of resistance occurs on the electrodes (3, 4) which is correlated to the ammonia concentration. The resistance change returns to the start value when subjected to gasing with moist or dry air; that is, complete reversibility is provided.

Figure 2:
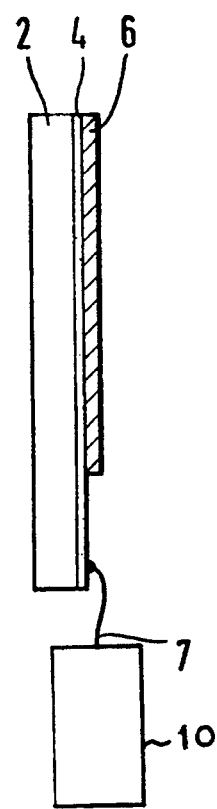
FIG. 2 is a side elevation view, in section, of the sensor of FIG. 1.

FIG. 2 shows a side elevation view of the sensor 1 with a view onto the connecting lead 7. The same components in FIG. 2 which correspond to those in FIG. 1 have the same reference numerals.

It is understood that the foregoing description is that of the preferred embodiments of the invention and that various changes and modifications may be made thereto without departing from the spirit and scope of the invention as defined in the appended claims.

What is claimed is:

1. A sensor for detecting an analyte in a fluid medium, the sensor comprising:
   a carrier;
   a pair of electrodes arranged on said carrier;
   a fullerene layer in contact with said electrodes and reversibly interacting with the analyte in the manner of an electron exchange to vary the conductivity of said layer in accordance with the concentration or the composition of said analyte; and,
   output means connected to said electrodes for supplying a signal indicative of said conductivity.

2. The sensor of claim 1, said electrodes being arranged on said carrier so as to have an interdigitated configuration; and, said fullerene layer comprising at least one of $C_{60}$-fullerene and $C_{70}$-fullerene.

3. The sensor of claim 1, said fullerene layer comprising at least one of the following: tetrahedral-symmetrical fullerene, octahedral-symmetrical fullerene, icosahedral-symmetrical fullerene; and/or said fullerene being at least one of a neutralized geometric tripole and a neutralized geometric dipole.

4. The sensor of claim 1, said fullerene layer having a thickness corresponding to 0.1 micrograms per square centimeter.

5. The sensor of claim 1, further comprising measuring means connected to said electrode pair for measuring a resistance change proportional to the quantity being measured; an said measuring means being selected from the group consisting of: a resistance measurement bridge, a constant voltage source and a constant current source.

6. The sensor of claim 1, wherein said fullerene layer is in the form of doped or substituted fullerene molecule structures having a charge state adapted to the organic or inorganic analyte in the fluid medium.

7. The sensor of claim 6, wherein the organic analytes are present as alkenes, alkyne, amine, aromatic hydrocarbons, alcohols, carbonyl compounds, halogenated hydrocarbons, heterocyclene, thioles, sulfide and nitrogen compounds and wherein the inorganic analytes are present as ammonia, hydrazine, phosphine, arsine, $H_2S$, halogens, nitrogen oxide and water.

8. A sensor for detecting an analyte in a fluid medium, the sensor comprising: a carrier, a pair of electrodes arranged on said carrier; a fullerene layer in contact with said electrodes and reversibly interacting with the analyte in the manner of an electron exchange to vary the conductivity of said layer in accordance with the concentration or the composition of said analyte;

a substance added to at least one of said fluid medium, said analyte and said fullerene for facilitating the interaction of said fullerene layer and said analyte so as to cause said analyte and said fullerene layer to have similar proton affinities; and, output means connected to said electrodes for supplying a signal indicative of said conductivity.

9. The sensor of claim 2, said substance being water vapor or water.

10. The sensor of claim 8, said fullerene layer being doped with a metal.

11. The sensor of claim 2, said electrodes being arranged on said carrier so as to have an interdigitated configuration; and, said fullerene layer comprising at least one of $C_{60}$-fullerene and $C_{70}$-fullerene.

12. The sensor of claim 8, said fullerene layer comprising at least one of the following: tetrahedral-symmetrical fullerene, octahedral-symmetrical fullerene, icosahedral-symmetrical fullerene; and said fullerene being at least one of a neutralized geometric tripole and a neutralized geometric dipole.

13. The sensor of claim 8, said fullerene layer having a thickness corresponding to 0.1 micrograms per square centimeter.

14. The sensor of claim 8, further comprising measuring means connected to said electrode pair for measuring a resistance change proportional to the quantity being measured; and, said measuring means being selected from the group consisting of: a resistance measurement bridge, a constant voltage source and a constant current source.

15. The sensor of claim 8, wherein said fullerene layer is in the form of doped or substituted fullerene molecule structures having a charge state adapted to the organic or inorganic analyte in the fluid medium.

16. The sensor of claim 15, wherein the organic analytes are present as alkenes, alkyne, amine, aromatic hydrocarbons, alcohols, carbonyl compounds, halogenated hydrocarbons, heterocyclene, thioles, sulfide and nitrogen compounds and wherein the inorganic analytes are present as ammonia, hydrazine, phosphine, arsine, $H_2S$, halogens, nitrogen oxide and water.

17. A sensor for detecting an analyte in a fluid medium, the sensor comprising:

a carrier;

a pair of electrodes arranged on said carrier;

a fullerene layer in contact with said electrodes and reversibly interacting with the analyte in the manner of an electron exchange to vary the conductivity of said layer in accordance with the concentration or the composition of said analyte;

output means connected to said electrodes for supplying a signal indicative of said conductivity; and, said fullerene layer being doped with a metal.

* * * * *

UNITED STATES PATENT AND TRADEMARK OFFICE
CERTIFICATE OF CORRECTION

PATENT NO. : 5,334,351

DATED : August 2, 1994

INVENTOR(S) : Jürgen Heinze and Andreas W. Synowczyk

It is certified that error appears in the above-identified patent and that said Letters Patent is hereby corrected as shown below:

In column 3, line 22: delete "$C_{60}NR_2R')_x$" and substitute -- $C_{60}(NR_2R')_x$ -- therefor.

In column 4, line 3: delete "unit" and substitute -- unit 10 -- therefor.

In column 4, line 54: delete "an" and substitute -- and, -- therefor.

Signed and Sealed this

Twenty-fifth Day of October, 1994

Attest:

BRUCE LEHMAN

*Attesting Officer*  *Commissioner of Patents and Trademarks*